US008882269B2

(12) United States Patent
Maor et al.

(10) Patent No.: US 8,882,269 B2
(45) Date of Patent: Nov. 11, 2014

(54) STRABISMUS DETECTION (71) Applicant: IRISS Medical Technologies Limited, London (GB)

(72) Inventors: Ron Uriel Maor, London (GB); Nigel Andrew Simon Barnard, London (GB); Yuval Yashiv, London (GB)

(73) Assignee: IRISS Medical Technologies Limited, London (GB)

( * ) Notice: Subject to any disclaimer, the term of this patent is extended or adjusted under 35 U.S.C. 154(b) by 0 days.

(21) Appl. No.: 14/349,745

(22) PCT Filed: Jul. 4, 2013

(86) PCT No.: PCT/GB2013/051771
§ 371 (c)(1),
(2), (4) Date: Apr. 4, 2014

(87) PCT Pub. No.: WO2014/023931
PCT Pub. Date: Feb. 13, 2014

(65) Prior Publication Data
US 2014/0268051 A1    Sep. 18, 2014

(30) Foreign Application Priority Data

Jul. 6, 2012 (GB) .................................. 1212093.7
Apr. 12, 2013 (GB) .................................. 1306713.7

(51) Int. Cl.
*A61B 3/08* (2006.01)
*A61B 3/10* (2006.01)
*A61B 3/00* (2006.01)
*A61B 3/14* (2006.01)

(52) U.S. Cl.
CPC .............. *A61B 3/085* (2013.01); *A61B 3/0008* (2013.01); *A61B 3/14* (2013.01)
USPC ........................... 351/202; 351/204; 351/246

(58) Field of Classification Search
USPC .................................................. 351/202, 204
See application file for complete search history.

(56) References Cited

U.S. PATENT DOCUMENTS 5,094,521 A    3/1992    Jolson et al.
5,355,895 A    10/1994   Hay
(Continued)

FOREIGN PATENT DOCUMENTS

WO    WO 2011/021936 A1    2/2011

OTHER PUBLICATIONS

Intellectual Property Office of the United Kingdom, Combined Search and Examination Report Under Sections 17 and 18(3), United Kingdom Patent Application No. 1212093.7, Nov. 1, 2012, 7 Pages.

(Continued)

*Primary Examiner* — Jordan Schwartz
(74) *Attorney, Agent, or Firm* — Fenwick & West LLP (57) ABSTRACT

A method for detecting strabismus in at least one image comprising a subject's eyes, wherein the at least one image has been obtained using an apparatus comprising a light source and a target offset from the light source, the method comprising, for each of the subject's left and right eyes: determining, from the image, a reflection offset distance, being the distance between a reference point of the eye and a reflection of a light source on the eye; determining a difference between the reflection offset distance and a reference reflection offset distance for the corresponding left or right eye, wherein the reference reflection offset distance has been determined based on relative positions of the light source, the target and the subject's head; and determining whether the difference is less than a difference threshold value for determining whether the subject has a strabismus.

19 Claims, 5 Drawing Sheets

(56) References Cited

U.S. PATENT DOCUMENTS

| | | | |
|---|---|---|---|
| 5,889,577 A * | 3/1999 | Kohayakawa | 351/211 |
| 6,616,277 B1 * | 9/2003 | Davenport | 351/221 |
| 6,663,242 B1 | 12/2003 | Davenport | |
| 2009/0153799 A1 | 6/2009 | Johns | |
| 2014/0085608 A1 * | 3/2014 | Clopton | 351/209 |

OTHER PUBLICATIONS

Marks&Clerk LLP, Response to Combined Search and Examination Report Under Sections 17 and 18(3), United Kingdom Patent Application No. 1212093.7, Jan. 8, 2013, 4 Pages.

Patent Cooperation Treaty, International Search Report and Written Opinion, International Patent Application No. PCT/GB2013/051771, Dec. 18, 2013, 7 Pages.

* cited by examiner

STRABISMUS DETECTION

RELATED APPLICATIONS

This application is the U.S. national phase of PCT/GB2013/051771 and claims foreign priority to United Kingdom application numbers GB1212093.7 filed Jul. 6, 2012, and GB1306713.7 filed Apr. 12, 2013, which are hereby incorporated by reference in their entirety for all purposes.

TECHNICAL FIELD

The invention relates to a method, apparatus and system for detecting strabismus in an image of a subject's eyes.

BACKGROUND

Detection of strabismus in subjects is typically performed manually. Under such circumstances, a trained clinician assesses a subject's eyes using the "Hirschberg test", which is a well-established, but rough, test for checking if the pupils of the eyes are symmetrical when in focus and fixating on a target placed directly in front of them.

Broadly speaking, the Hirschberg test is carried out by shining a light at the eyes of a subject from a light source positioned directly in front of the eyes, getting the patient to focus on the light or an object right next to it, and seeing whether the distance between the reflection of the light and the centre of the pupil appears to be equal in magnitude and direction in both eyes.

Small differences in each of the eyes of a subject are difficult to determine manually and are therefore easy to miss, even by experienced clinicians. Typically, differences of anything less than about 1 mm are too small to see reliably. Difficulties with the test are exacerbated when the subject is a small child, as it is hard to get a child to fixate and focus on a target for long enough to assess each eye. Therefore, the decision of whether the eyes are symmetrical is often made quickly and without complete information. It is also a test that requires considerable skill, and no is impractical for many testing scenarios, such as testing all pre-school children in a given territory.

SUMMARY

According to the invention in a first aspect, there is provided a method of processing at least one image for detecting strabismus. The at least one image has been obtained using an apparatus comprising a light source and a target offset from the light source. For each of the subject's left and right eyes, a reflection offset distance, being the distance between a reference point of the eye and a reflection of a light source on the eye, is determined. A difference between the reflection offset distance and a reference reflection offset distance for the corresponding left or right eye is determined. The reference reflection offset distance has been determined based on relative positions of the light source, the target and the subject's head. It is determined whether the difference is less than a difference threshold value.

Optionally, the image has been obtained using an apparatus in which the light source and the target are positioned in a device plane perpendicular to an axis defining the direction that the subject is facing.

Optionally, the image has been obtained using an apparatus in which one of the light source and the target is positioned in front of the subject on the axis defining the direction that the subject is facing, such that the target, the light source and the subject's head form a right angled triangle.

Optionally, the image has been obtained using an apparatus in which the light source is positioned on the axis defining the direction that the subject is facing.

Optionally, the method further comprises obtaining the image.

Optionally, the target comprises an attention grabber, and obtaining the image comprises operating the attention grabber to attract the subject's attention such that the subject's eyes fixate on the target.

Optionally, the image is obtained while the attention grabber is operating.

Optionally, the attention grabber comprises one or more of a light, a flashing light and a means for generating a sound.

Optionally, the method further comprises instructing the subject to fixate their eyes on the target.

Optionally, the reference reflection offset distance has been determined based on a distance from the light source to the target and a distance from the light source or the target to the subject's head.

Optionally, the reference reflection offset distance has been determined based on the distance from the device plane to the subject's head along the axis defining the direction that the subject is facing.

Optionally, the method further comprises determining the reference reflection offset distance.

Optionally, the reference point of the eye comprises the centre of the pupil of the eye.

Optionally, the method further comprises determining that no strabismus is present in the image of the subject's eyes if the difference is less than the difference threshold.

Optionally, the at least one image comprises a plurality of images, and each of the plurality of images has been obtained with the target in a different location relative to the light source.

Optionally, the plurality of images has been obtained with the target at a plurality of angularly spaced locations relative to the light source.

Optionally, the plurality of angularly spaced locations are equally angularly spaced.

Optionally, the method further comprises determining whether the number of images in which the difference is less than the difference threshold value is greater than an image threshold value.

Optionally, the method further comprises, if the number of images is greater then the image threshold value, determining that the subject does not have a concomitant squint.

Optionally, the difference threshold value is a lower threshold value, and the method further comprises, if the difference is greater than the lower threshold value, determining whether the difference is greater than an upper threshold value.

Optionally, the method further comprises determining that the subject is not looking at the target if the difference is greater then the upper threshold.

According to the invention in a second aspect, there is provided a computer program product comprising computer program code configured, when run on a computer, to undertake the method described herein.

According to the invention in a third aspect, there is provided an apparatus comprising a processor configured to carry out the method described herein.

Optionally, the apparatus further comprises a camera and a light source, each in electrical communication with the processor, wherein the camera is configured to obtain an image while the light source is emitting light.

According to the invention in a fourth aspect, there is provided a system for processing at least one image for detecting strabismus, the system comprising: a camera; a light source; a target offset from the light source; and a processor in electrical communication with the camera and the light source, wherein the camera is configured to capture an image while the light source is emitting light, and wherein the processor is configured to carry out the method described herein.

According to the invention in a fifth aspect, there is provided a kit of parts comprising: an apparatus as described herein; and a target.

According to the invention in a sixth aspect, there is provided a device for processing at least one image for detecting strabismus, the image obtained using an apparatus comprising a light source and a target offset from the light source, the device comprising: an input interface configured to receive image data from a camera; a memory for storing image data received from the camera; and a processor configured to process the image data, for each of the subject's left and right eyes, by determining, in the image data, a reflection offset distance, being the distance between a reference point of the eye and a reflection of a light source on the eye, determining a difference between the reflection offset distance and a reference reflection offset distance for the corresponding left or right eye, wherein the reference reflection offset distance has been determined based on a relative position of the light source, the target and the subject's head, and determining whether the difference is less than a difference threshold value.

Optionally, the device further comprises a camera configured to obtain the image data and transmit the image data to the input interface.

Optionally, the device further comprises a light source, wherein the camera is configured to obtain the image data while the light source is emitting light.

Optionally, the device further comprises a display, configured to display to a user information relating to whether the subject has a strabismus.

BRIEF DESCRIPTION OF THE DRAWINGS

Exemplary embodiments of the invention will now be described with reference to the accompanying drawings, in which.

DESCRIPTION

Generally, disclosed herein is a method, apparatus and system for detecting strabismus in an image of a subject's eyes, the image being captured by a camera using a light source and a target that is offset from the light source. The offset target provides a focal point for a subject, who may be instructed (or attracted by a light and/or a sound) to look at the target when an image is captured. Through knowledge of the relative position of the subject, the light source and the target, reference data may be determined that may be compared with data determined from the captured image for detecting strabismus.

During a manual Hirschberg test, a subject focuses on a light source located directly to their front and a clinician assesses the relative separation between the reflection of the light source and the centre of the pupil in each eye. This process may be automated by capturing an image and performing image processing techniques. The inventors have appreciated that a problem exists with this type of strabismus detection if a subject relaxes their eyes during the test. Subjects, children in particular, normally do not fixate and focus on a given location for long periods so, when the test is undertaken, their eyes are often relaxed and "staring into the middle distance". If a Hirschberg test is undertaken in an automated system, without a skilled clinician, this causes a problem as the automated system is unable to distinguish between eyes focused and fixated on a correct location and eyes that are relaxed. When a subject's accommodation (focus) is relaxed, a strabismus that would otherwise be evident may not be seen. Additionally, when a subject's eyes do not fixate, they fall to a position looking directly to the front. Therefore, using a typical Hirschberg test, if a subject relaxes their eyes, e.g. when they are "day dreaming", they may appear to be looking directly ahead and to have no strabismus, which leads to an increased number of false negatives resulting from the test.

Figure 1A:
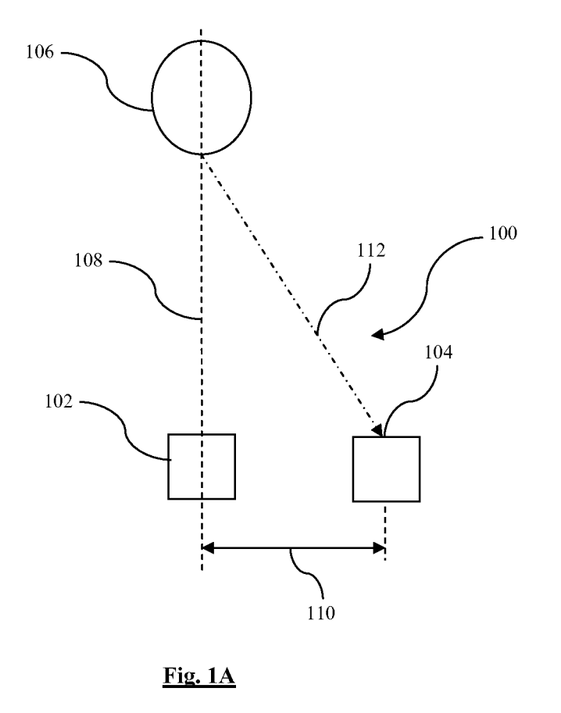
FIG. 1A is a schematic representation of a system for detecting strabismus in a subject.

FIG. 1A shows schematically a system 100 for detecting strabismus. The system 100 comprises a light source 102 and a target 104. The light source 102 may, for example be a flash used in a camera assembly. In the exemplary system 100 of FIG. 1A, the light source 102 is directly in front of a subject's head 106. That is, the subject's head 106 faces the light source 102 to define an axis 108. The axis 108 extends through the centre of the subject's head in a forward direction from the face of the subject and passes through the centre of the light source 102.

The target 104 is offset from the light source 102 in a direction perpendicular to the axis 108 by a distance 110. In exemplary systems, the target may be offset from the light source by a distance in the range from 5 cm to 10 cm.

The inventors have appreciated that the problem defined above may be solved if the subject focuses on the offset target during the test. In the system 100 of FIG. 1A, the subject's head 106 remains aligned with the axis 108, while the subject's eyes are rotated to a line of sight shown by dashed line 112. In this way, the problem of relaxation of a subject's eyes is overcome as relaxed eyes always fall to a position looking directly ahead, which will be immediately obvious during the test. That is, if the subject begins to daydream, their eyes will relax to look along the axis 108.

Figure 1B:
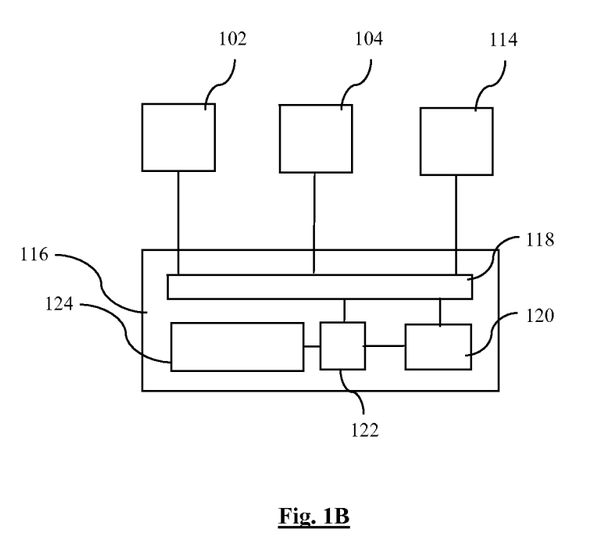
FIG. 1B is a block schematic representation of a system for detecting strabismus in a subject.

The system also includes a camera (114 in FIG. 1B), which may be collocated with the light source 102, and a processor (122 in FIG. 1B). The camera may alternatively be located at other positions in other exemplary systems. In addition, it is noted that in other exemplary systems, the subject's head may face a target and the eyes may be rotated to focus on a light source. Indeed, in alternative systems, a subject's head, a light source, a target and a camera may have any relative positions so long as those relative positions are known or measured and may be defined by one or more distances and/or angles.

A block schematic of the system 100 is shown in FIG. 1B. The light source 102, the target 104 and a camera 114 are in electrical communication with a device 116. More specifically, the light source 102, the target 104 and a camera 114 are in electrical communication with an input interface 118 of the device 116. The target 104 is shown in FIG. 1B in electrical communication with the device 116 via the input interface 118 as the target may transmit and receive data to and from the device 116. For example, the target 104 may provide an attention grabber, such as a flashing light or image or a sound, to encourage a subject to focus on the target, which attention grabber may be controlled by the device 116. In addition, the target 104 may include one or more sensors configured to collect data and transmit that data to the device 116. However, it is noted that the target 104 is not required to be in electrical communication with the device 116 and can be any object offset from the light source 102.

The device 116 also comprises a memory 120 for storing data received from the light source 102, the target 104 or the camera 114. To this end, the memory 120 is in electrical communication with the input interface 118.

The device 116 also comprises a processor 122 for processing data stored in the memory 120. In particular, the processor 122 is configured to process image data received from the camera 114 and stored in the memory 120. The operation of the processor 122 in processing the image data is discussed in greater detail below.

The device also comprises a display 124 for displaying information to a user of the device 116. The display 124 may, for example, be configured to display the results of a test for determining whether a subject has a strabismus as set out below. In certain embodiments, the display 124 may also be configured to receive inputs from a user via a touch surface. Other devices may allow input by a user through other means, such as a keyboard.

The electrical communications are shown as physical links in FIG. 1B, but it is noted that the electrical communications may be provided by other means, such as a wireless communications system or a network.

In the exemplary system described herein, the light source 102 is collocated with the camera 114 in a single device 116. In addition, the processor 122 is collocated with the light source 102 and the camera 114 in the same device 116. The device 116 may be a camera, a smart-phone, a FDA, a laptop, ophthalmoscope or any other device capable of capturing images and comprising a processor capability. However, it is noted that, in other exemplary systems, each of the light source 102, the camera 114 and the processor 122 may be located in separate devices. In a particular exemplary system, the light source 102 and the camera 114 may be included in a single device, further configured to store captured images. The captured images may then be transferred to a separate device comprising a processor, which is configured to process the captured images as disclosed herein.

Figure 2:
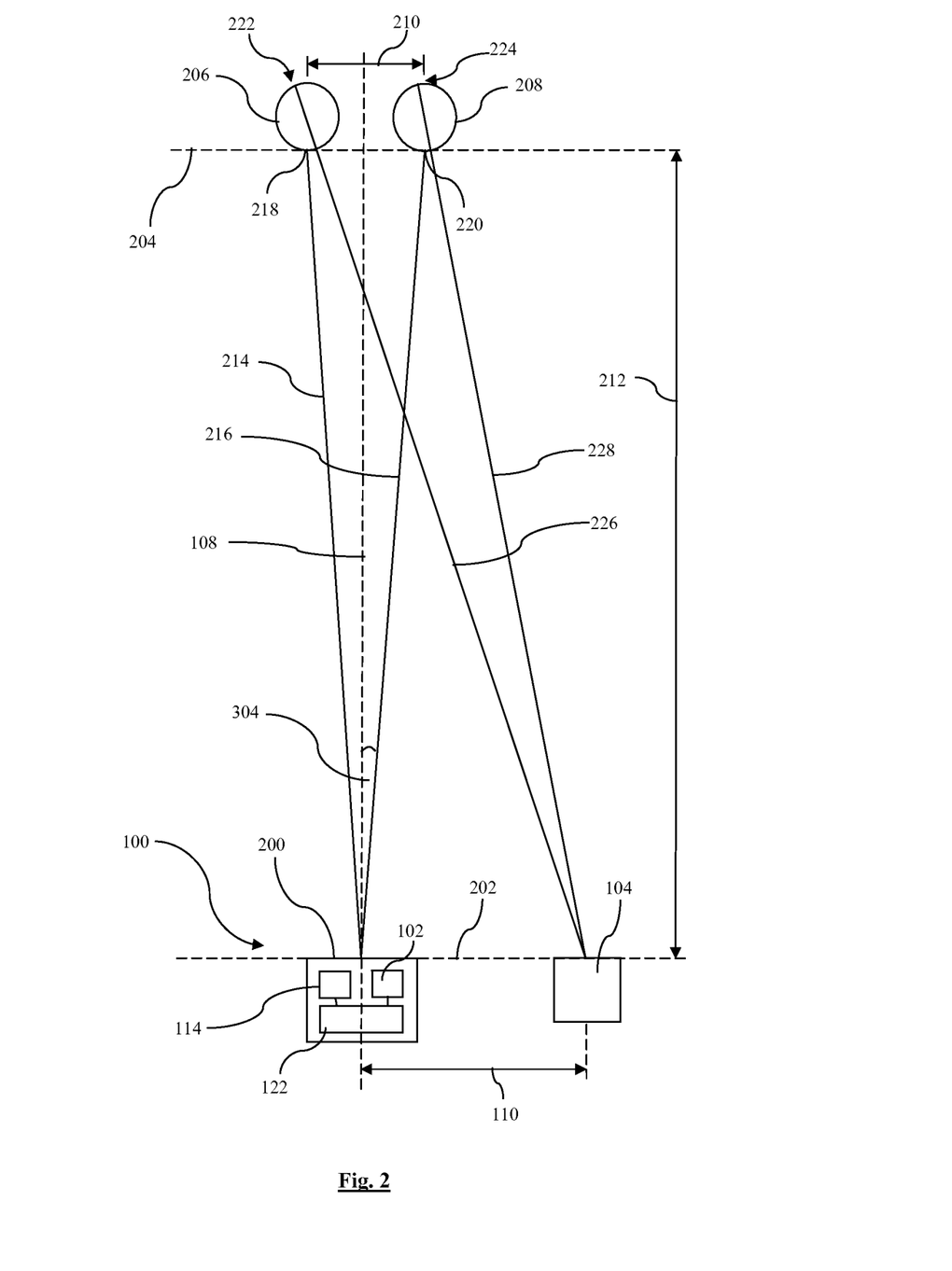
FIG. 2 is a schematic of a layout of a system for detecting strabismus in a subject.

FIG. 2 shows an exemplary system 100 for detecting strabismus. The system comprises a device 200 comprising the camera 114, the light source 102 and the processor 122. The target 104 is offset from the device 200 by the distance, $d_{l-t}$, 110. The device 200 and the target 104 are each located in a device plane defined by the dashed line 202, which is perpendicular to the axis 108 and parallel to a face plane defined by dashed line 204. The face plane 204 is the plane defined by the face of the subject, shown schematically in FIG. 2 to be across the front of a right eye 206 and a left eye 208 of a subject.

The right eye 206 and the left eye 208 are separated by a distance, $d_{eyes}$, 210. The device 200, and more specifically the light source 102 and the camera 114, are centred between the right eye 206 and the left eye 208 and positioned a distance, $d_{d-f}$, 212 away from the plane 204. In practice, the distance, $d_{d-f}$, 212 may not be defined as accurately as depicted in FIG. 2 and may, for example, be measured simply as the distance from the light source to the subject's head. However, the distance, $d_{d-f}$, 212 is typically in the range from 0.5 meters to 3 meters and no inaccuracies in the measurement of the distance, $d_{d-f}$, 212 will not impact greatly on the determination of the reference reflection offset (described below). In other exemplary embodiments, the distance $d_{d-f}$ 212 may be measured by the camera 114.

The light source 102 is configured to emit light toward the eyes 206, 208 along lines 214 and 216. This results in light source reflections seen at the positions 218, 220 on the eyes 206, 208 where the emitted light 214, 216 contacts the eyes 206, 208. The light source is reflected from the cornea of the eyes 206, 208.

The eyes 206, 208 view the target 104 using the fovea 222, 224, the central part of the macula at the back of the eyes 206, 208. The fovea 222, 224 view the target 104 through the pupils of the eye (shown in FIG. 3) along a lines of sight 226, 228.

Figure 3:
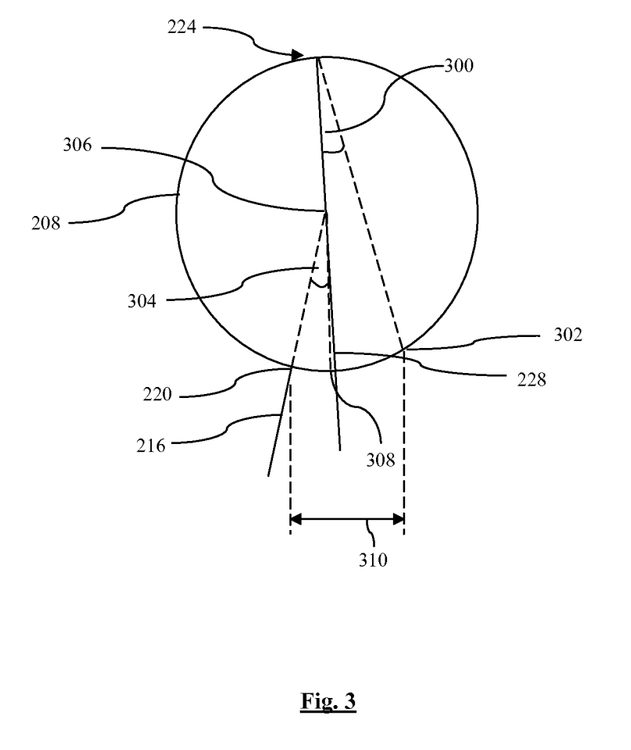
FIG. 3 is an enlarged schematic of the left eye of FIG. 2.

FIG. 3 shows a close up schematic view of the left eye of FIG. 2. Corresponding features of FIG. 3 that also appear in FIG. 2 are given the same reference numerals.

An angle, kappa, 300 is defined between the line of sight 228 and a line taken from the fovea 224 and the centre of the pupil 302. The angle kappa is a known angle within the field of ophthalmology and is therefore known to the skilled person. Typically, the angle kappa is approximately three degrees for a majority of subjects. In exemplary apparatuses and methods disclosed herein, the angle kappa may be assumed to be three degrees, or some other average value of kappa for a particular population. In other exemplary apparatuses and methods, the angle kappa may have been measured previously for a subject and that measured value may be used. In addition, an angle, alpha, 304 may be defined at a centre 306 of the eye 208 between a notional mid-point 308 of the eye 208 and the light source reflection point 220. Alpha 304 is also shown in FIG. 2 between the axis 108 and the line of sight 216. Alpha 304 shown in FIG. 2 has the same value as alpha 304 shown in FIG. 3 as they are corresponding angles. The notional mid-point 308 of the eye 208 is the point at which a line taken from the centre point 306 and parallel to the axis 108 intersects the surface of the eye 208. This notional mid-point 308 aids in the calculation of reference data as set out below.

Referring to FIGS. 2 and 3, reference data may be determined representing the expected reflection offset distance 310 in a non-strabismic eye. The reflection offset distance 310 being the distance between the centre of the pupil 302 and the light source reflection 220. An exemplary method of calculating a reference reflection offset distance 310 is net out below for the left eye 208. A similar method may be arrived at for the right eye 206.

Alpha 304 is determined by:

$$\alpha = \tan^{-1}\left(\frac{\frac{d_{eyes}}{2}}{d_{d-f}}\right)$$

This assumes that the distance $d_{d-f}$ is equal to the distance from the device plane 202 to the centre 306 of the eye 208, which is a safe assumption if $d_{d-f}$ is much greater than the radius of the eye 208. The straight line distance, $d_{r-m}$, between the light source reflection 220 and the notional mid-point 308 is then determined by:

$$d_{r-m} = \tan(\alpha) r$$

where r is the radius of the eye 208, i.e. the distance from the centre 306 to the notional mid-point 308.

An angle, beta, may be defined between the line of sight 228 and a straight line parallel to the axis 108 and connecting the left fovea 224 to the device plane 202. Assuming that the fovea 224 is directly behind the centre 306 of the eye 208, which is a safe assumption if $d_{d-f}$ is large relative to r and the angle of the line of sight is sufficiently small, the angle beta may be determined by:

$$\beta = \tan^{-1}\left(\frac{d_{l-1} - \frac{d_{eyes}}{2}}{d_{d-f}}\right)$$

Now, the distance between the notional mid-point 308 on the surface of the eye 208 and the centre of the pupil 302 may be determined by:

$$d_{m-p} = \sin(\beta + \kappa)d$$

where d is the diameter of the eye 208.

The reference reflection offset distance is therefore determined by:

$$d_{roffset} = d_{r-m} + d_{m-p}$$

The above describes one exemplary method for determining the reference reflection offset. It is noted that many other methods may be employed using basic trigonometric functions. The method described above makes certain assumptions, which improve the speed of the calculation without having a significant impact on the determined reference reflection offset value. The assumptions are based on the fact that the distance, $d_{d-f}$, 212 is much greater than the distances in the area of the subject's face, e.g. the radius of the eye, and that the angles of the lines of sight 226, 228 to the axis 108 are small. However, more accurate methods of determining the reference reflection offset may be used if such assumptions become unsafe, i.e. if the relative magnitude of the distance, $d_{d-f}$, 212 and the distances in the area of the subject's face, e.g. the radius of the eye, and the angles of the lines of sight 226, 228 to the axis 108 begin to affect significantly the accuracy of the reference reflection offset distance.

When conducting a test to detect strabismus, a subject is instructed to face the light source 102 and direct their eyes 206, 208 to and focus on the target 104. An image is then taken by the camera 114.

Figure 4:
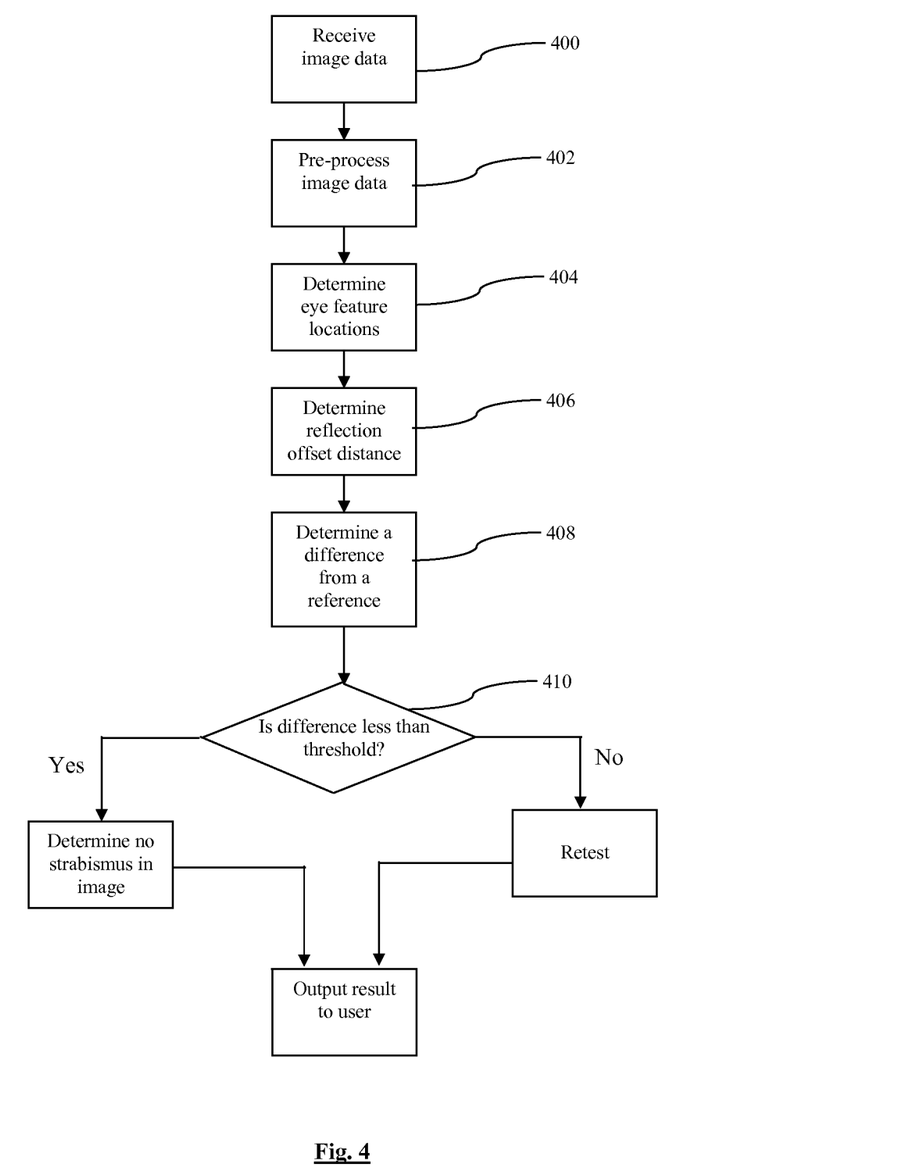
FIG. 4 is a flow chart showing a method for detecting strabismus in a subject.

Referring to FIG. 4, an exemplary method of processing the image for the detection of strabismus is shown.

Reference data, which may form part of a look-up table, is provided that includes data indicative of pixel values (e.g. intensities and colours) associated with different features within a subject's face, and data indicative of pixel values associated with different features within a subject's eye region. For example, the reference data may include ranges for RGB values typical for various skin types, ranges for RGB values typical for sclera pixels, ranges for RGB values typical for pupil pixels, etc.

Image data is received 400 by the processor 122 from the memory 120. The processor 122 pre-processes 402 the image data to determine whether it comprises both the left and right eyes 206, 208 of the subject and to determine the location of the eyes 206, 208. To this end, the processor 122 uses the reference data described above to determine whether the pixels of the image data comprise pixels relating to left and right eye regions of the subject.

Once it is determined that the image data includes the eyes 206, 208 of the subject, the accurate locations of the eye features are determined 404. In order to determine accurate locations for the eye features, the processor 122 re-classifies the pixels within the image data and processes and analyses this data. More specifically, in a non-limiting example of the invention, relative brightness of the pixels is used to determine, for each eye 206, 208, accurate parameter values for the centre of the light source reflection 218, 220 and the centre of the pupil 302. In exemplary systems, the processor 122 is configured to locate the centre of the light source reflection 218, 220 and the centre of the pupil 302 for each of the left and right eyes 206, 208.

A rough location of each of the eyes 206, 208 is determined, by grouping and counting adjacent pixels associated with different parts/features of each eye region, e.g. pupil and sclera zones. A weighted centre of these pixels is calculated, which is taken to be the rough centre of the eye 206, 208. A rectangle is defined around each weighted centre having a width four times larger than its height and covering an area four times the number of pixels in each eye region.

The pixels are re-classified within the rectangle using a reclassification technique based on the RGB values for pixels of different features in the eye region. More specifically, in each eye region, a count is performed of the pixels by their RGB values considering that in a typical eye region there are pixels related to sclera, having RGB values of about 200,200,200, and pixels related to eyelashes or pupil, having RGB values of about 30,15,15. It should be understood that these values, and similar values mentioned below, are not limiting examples of the reference data.

Also, the brightest pixels are identified within each rectangle (eye region) of the left and right eyes 206, 208 in order to locate the light source reflection 218, 220. These pixels may have RGB values of approximately 254,252,250.

The processor 122 counts the number of the brightest pixels, which relate to the light source reflection 218, 220, and calculates rough weighted centres of the light source reflections 218, 220 in each eye. Then, a rough radius of the light source reflection 218, 220 (being large enough to cover the light source reflection 218, 220) is determined as a square root of the number of the light source reflection pixels and a bounding square region is defined around each light source reflection 218, 220 having sides twice the size of the radius.

The rough values of the centre and radius parameters of the light source reflection 218, 220 are used to arrive at more accurate values, as follows.

Within each bounding square, pixels are re-classified according to the corresponding reference data about typical values of light source reflection pixels, light source reflection boundary pixels typically having values intermediate between very bright and very dark, and other pixels. A more precise weighted light source reflection 218, 220 centre is calculated for each eye 206, 208 using the brightness of the light source reflection pixels as their weight. When calculating the weighted centre, a bright pixel counts as one pixel and a boundary pixel counts as less than one pixel, in proportion to how bright it is. Thus, a pixel that is halfway between fully bright and fully dark will be counted as half a pixel. The newly calculated centre in pixel units may or may not be an integer.

Then, the centre of the pupil zone of each eye is located in the rectangle region. The light source reflection 218, 220 is removed from the rectangle. The processor 122 therefore makes a copy of the rectangle region and processes that copied image to remove the light source reflection 218, 220 therefrom and replace the respective pixels by pixels related to the pupil. The pixels associated with the area covered by the light source reflection 218, 220 are now assigned with RGB values being a weighted average of other eye-part pixels nearby. Each of the replaced pixels is assigned with the RGB value of the nearest pixel outside the light source reflection 218, 220, resulting in a rough replacement of the light source reflection 220 by the pupil and iris zones.

The replacement pixels within the removed light source reflection 218, 220 are re-classified as corresponding to pupil, iris, sclera and other (including skin, eye lashes, etc.) as indicated above utilizing the corresponding reference data.

More specifically, dark pixels in each eye region are classified as pupil-related pixels having RGB values of about 12, 12, 12, and the number of these pixels is determined. Then, a weighted centre of these dark pixels is determined and considered as a rough centre of the pupil. A rough radius of the pupil, being large enough to cover the pupil zone, is determined as a square root of the number of pupil associated pixels and a square having a side of twice the radius is defined as surrounding the rough centre.

The pixels in the bounding square are reclassified as "pupil pixels" (typically very dark), "pupil border pixels" (typically having slightly brighter values) and "other pixels". A weighted centre is calculated using this classification where the pupil border pixels are given a weight proportional to their darkness. The result is considered as an accurate centre of the pupil 302 for each eye, which may or may not be an integer in pixel units.

The centre of the pupil 302 of each eye is used as a reference point within the eye to determine 406, for each eye, the reflection offset distance 310, i.e. the distance between the light source reflection 218, 220 and the centre of the pupil 302. It is noted that other points in the image may be used as a reference point for determining the reflection offset distance 310. For example, a retinal reflex, which is a reflection of light of the retina of the eye may be used as a reference point to determine the reflection offset distance 310. As explained below, a light source used in exemplary methods and apparatus may emit light having any wavelength and this light may therefore be used to generate a retinal reflex. For example, in specific exemplary methods and apparatus, the retinal reflex may be generated using visible light or infrared light.

The determined reflection offset distance 310 is compared to the reference reflection offset distance described above to calculate a difference between the two 408.

It is then determined 410 whether the difference is less than a difference threshold value, which can be used to determine whether the subject has a strabismus. In particular, if the difference is less than the difference threshold, the system 100 determines that the subject does not have a strabismus.

Exemplary difference threshold values may be in the range from 0.07 mm to 0.13 mm. A particular exemplary difference threshold value is 0.1 mm.

The result of the determination 410 is output to the user via the display 124.

If the difference is determined to be greater than the difference threshold value, this may indicate either that the subject is not looking at the target, or that the subject is strabismic and is looking at the target. Therefore, if the difference is greater than the difference threshold value, the system 100 may output an indication to the user that the test must be conducted again.

Figure 5:
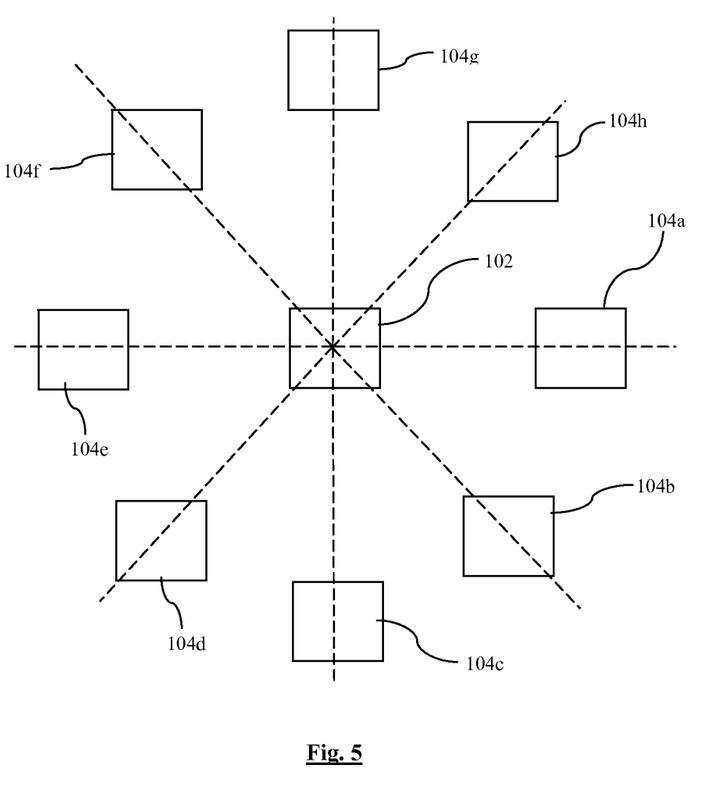
FIG. 5 shows a system for detecting strabismus in a subject.

Referring to FIG. 5, an arrangement of a system is shown with the target 104 in a plurality of locations with respect to the light source 102. In FIG. 5, a plurality of targets 104a to 104h are shown at different locations in the device plane 202. However, it is noted that the system may comprise only a single target 104 that is movable to each of the different locations. The device plane 202 is parallel to the sheet of paper on which FIG. 5 is drawn.

In the exemplary system of FIG. 5, eight targets 104a to 104h are positioned equally angularly spaced with respect to the light source 102. In addition, the distance from the light source 102 to each of the targets 104a to 104h is the same. As a result, the targets 104a to 104h are located on the circumference of a notional circle with the light source 102 at the centre. It is noted that alternative exemplary systems may have other numbers of targets and/or other target arrangements.

When determining whether a subject has a strabismus using the system of FIG. 5, eight images are obtained and are each processed as disclosed above. In each of the eight images, a subject fixates their eyes on a different one of the targets 104a to 104h. In the exemplary system of FIG. 5, the same reference reflection offset distance may be used for each captured image as the distance between the light source 102 and each of the targets 104a to 104h is the same. Alternatively, a different reference reflection offset distance may be determined for each image.

In particular, the determination of different reference reflection offset distances may be required in systems in which the distance between the light source 102 and each of the targets 104a to 104h are not the same. In such cases, the principles of determining the reference reflection offset that are described above apply for each image with values changed, as necessary.

The use of the system of FIG. 5 allows the detection of a concomitant squint in a plurality of images. A concomitant squint is one in which an affected eye has a squint in every direction that the subject looks. All the eye muscles are working properly, and therefore it is also called a non-paralytic squint. With a concomitant squint the subject's eyes always face in different directions. As the system of FIG. 5 obtains a plurality of images, each with the subject looking in a different direction, the existence of a concomitant squint may be determined.

In exemplary systems and methods, an image threshold may be used whereby, if a number of images in which the difference is less than the lower difference threshold is greater than the image threshold, it is determined that the subject does not have a concomitant squint.

In the exemplary system of FIG. 5, the image threshold may be five images. In other exemplary systems, the image threshold may be greater than 50% of the number captured images.

Exemplary systems and methods may comprise a lower difference threshold (defined above) and an upper difference threshold value that is higher than the lower threshold value mentioned above. The upper threshold value is for determining whether the subject is looking at the target or not. That is, if the difference between the determined reflection offset distance and the reference reflection offset difference is so great that it is greater than the upper threshold, this indicates that the subject must not have been looking at the target. Therefore, if the difference is greater than the upper threshold value, the user is instructed to undertake another test as described above and the results of the current test are discarded.

In exemplary systems, the processor 122 may determine the reference reflection offset distance 310 based on the relative positions of the light source 102, the target 104 and the subject. This information may be provided by a user of the system, who may measure the respective distances between the light source 102, the target 104 and the subject and input those distances to the processor. The processor may then determine the reference reflection offset distance 310 as part of the method of FIG. 4.

However, it is noted that it is not an essential feature of the systems and methods disclosed herein that the processor 122 determines the reference reflection offset distance 310. In exemplary systems and methods, images may be captured while the system is arranged to a predetermined layout with respect to the subject. That is, the distance between the light source 102 and the target 104 and the distance between the face plane 202 and the device plane 204 may be predefined and the system 100 may be arranged to that predefined layout. In such cases, the reference reflection offset distance 310 may be calculated in advance and supplied to the processor.

Exemplary systems may comprise a device that includes a camera part configured to take pictures in conjunction with a light source, such as a camera flash, and a fixation target, such as a colourful flashing LED light. In exemplary systems the fixation target does form part of on the camera part itself, but is offset to one side by a distance, typically in the range from 5 to 10 centimeters. The camera part may be equidistant from each eye, typically facing the patient straight on.

It is noted that the taking of an image of a subject is not an essential feature of the systems and methods disclosed herein. In exemplary systems, images may have been taken previously and at locations remote from the processor and may be transmitted to the processor for detecting strabismus.

It is noted that the term "camera" encompasses any camera or sensor configured to detect electromagnetic radiation in any part of the electromagnetic spectrum. Accordingly, the camera may be configured to capture images using electromagnetic radiation in any part of the electromagnetic spectrum. Accordingly, the camera may comprise one or more sensors for detecting electromagnetic radiation in any part of the electromagnetic spectrum.

In specific methods and apparatus disclosed herein, the camera may be configured to capture images using the light spectrum, which encompasses infrared light, visible light and ultraviolet light. Accordingly, the camera may comprise one or more sensors for detecting one or more of infrared electromagnetic radiation, visible electromagnetic radiation and ultraviolet electromagnetic radiation.

In addition, a light source used in exemplary methods and apparatus may be configured to emit electromagnetic radiation corresponding to the electromagnetic radiation sensed by the camera. If the camera is configured to capture images using infrared electromagnetic radiation, a light source may be configured to emit infrared electromagnetic radiation and similarly for visible electromagnetic radiation and ultraviolet electromagnetic radiation. In exemplary methods and apparatus, the light source 102 that is offset from the target 104 may be configured to emit infrared light. Alternatively, the light source 102 may be configured to emit visible light and the system 100 may comprise one or more further light source that are configured to emit infrared and/or ultraviolet light. The one or more further light sources may be arranged to generate a retinal reflex detectable by the camera 114.

In other exemplary apparatus and methods, the light source 102 may be configured to emit continuous infrared light and to generate a retinal reflex and a corneal reflex on the eye of a subject. The camera 114 may be operated to obtain an infrared image of the subject's eye and the retinal reflex and/or the corneal reflex may be used to determine whether the image is indicative of a strabismus.

Advantageously, the infrared images disclosed herein may be captured in dark conditions such that pupil dilation (and therefore the retinal reflex) is increased.

As used herein, the term "infrared electromagnetic radiation" encompasses electromagnetic radiation having a frequency in a range from 300 GHz to 400 THz (a wavelength in the range from 1 mm to 750 nm). Further, infrared radiation may be split into three subgroups: far-infrared, which encompasses electromagnetic radiation having a frequency in a range from 300 GHz to 30 THz (a wavelength in the range from 1 mm to 10 μm); mid-infrared, which encompasses electromagnetic radiation having a frequency in a range from 30 THz to 120 THz (a wavelength in the range from 10 μm to 2.5 μm); and near-infrared, which encompasses electromagnetic radiation having a frequency in a range from 120 THz to 400 THz (a wavelength in the range from 2.5 μm to 750 nm).

As used herein, the term "visible electromagnetic radiation" encompasses all light visible to the human eye, which includes electromagnetic radiation having a frequency in a range from 400 THz to 790 THz (a wavelength in the range from 750 nm to 380 nm).

As used herein, the term "ultraviolet electromagnetic radiation" encompasses electromagnetic radiation having a frequency in a range from 30 PHz to 790 THz (a wavelength in the range from 10 nm to 380 nm).

It is further noted that the term "image" as used herein encompasses video data and still image data. Accordingly, the methods and apparatus disclosed herein may be implemented using video data and/or still camera image data. That is, the camera may be configured to capture video data and/or still image data. Further, methods may be undertaken on video data and/or still image data. The video data and the still image data may be captured using electromagnetic radiation in any part of the electromagnetic spectrum, as set out above.

In addition, it is noted that the methods and apparatus disclosed herein

The skilled person will be able to envisage further embodiments of the invention without departing from the scope of the invention as defined in the appended claims. In particular, although the invention has been described with reference to determining strabismus, it will be appreciated that it may be possible to apply it to other eye conditions.

The invention claimed is:

1. The method of processing at least one image for detecting strabismus, wherein the at least one image has been obtained using an apparatus comprising a light source and a target offset from the light source, the method comprising, for each of the subject's left and right eyes:
   determining, from the image, a reflection offset distance, being the distance between a reference point of the eye and a reflection of a light source on the eye;
   determining a difference between the reflection offset distance and a reference reflection offset distance for the corresponding left or right eye, wherein the reference reflection offset distance has been determined based on relative positions of the light source, the target and the subject's head; and
   determining whether the difference is greater than a difference threshold value for detecting strabismus.

2. The method according to claim 1, wherein the image has been obtained using an apparatus in which the light source and the target are positioned in a device plane perpendicular to an axis defining the direction that the subject is facing.

3. The method according to claim 2, wherein the image has been obtained using an apparatus in which one of the light source and the target is positioned in front of the subject on the axis defining the direction that the subject is facing, such that the target, the light source and the subject's head form a right angled triangle.

4. The method according to claim 3, wherein the image has been obtained using an apparatus in which the light source is positioned on the axis defining the direction that the subject is facing.

5. The method according to claim 1, wherein the target comprises an attention grabber, and wherein obtaining the image comprises operating the attention grabber to attract the subject's attention such that the subject's eyes fixate on the target.

6. The method according to claim 1, wherein the reference reflection offset distance has been determined based on a distance from the light source to the target and a distance from the light source or the target to the subject's head.

7. The method according claim 2, wherein the reference reflection offset distance has been determined based on the distance from the device plane to the subject's head along the axis defining the direction that the subject is facing.

8. The method according to claim 1, wherein the at least one image comprises a plurality of images, and wherein each of the plurality of images has been obtained with the target in a different location relative to the light source.

9. The method according to claim 8, further comprising determining whether the number of images in which the difference is less than the difference threshold value is greater than an image threshold value.

10. The method according to claim 9, further comprising, if the number of images is greater than the image threshold value, determining that the subject does not have a concomitant squint.

11. The method according to claim 1, wherein the at least one image has been obtained by the detection at least one of: infrared electromagnetic radiation, visible electromagnetic radiation and ultraviolet electromagnetic radiation.

12. The method according to claim 1, wherein the at least one image comprises at least one of video data and still image data.

13. A computer program product comprising computer program code configured, when run on a computer, to undertake the method for processing at least one image for detecting strabismus, wherein the at least one image has been obtained using an apparatus comprising a light source and a target offset from the light source, the method comprising, for each of the subject's left and right eyes:
   determining, from the image, a reflection offset distance, being the distance between a reference point of the eye and a reflection of a light source on the eye;
   determining a difference between the reflection offset distance and a reference reflection offset distance for the corresponding left or right eye, wherein the reference reflection offset distance has been determined based on relative positions of the light source, the target and the subject's head; and
   determining whether the difference is greater than a difference threshold value for detecting strabismus.

14. An apparatus comprising:
   a processor configured to carry out a method for processing at least one image for detecting strabismus, wherein the at least one image has been obtained using an apparatus comprising a light source and a target offset from the light source, the method comprising, for each of the subject's left and right eyes:
      determining, from the image, a reflection offset distance, being the distance between a reference point of the eye and a reflection of a light source on the eye;
      determining a difference between the reflection offset distance and a reference reflection offset distance for the corresponding left or right eye, wherein the reference reflection offset distance has been determined based on relative positions of the light source, the target and the subject's head; and
      determining whether the difference is greater than a difference threshold value for detecting strabismus.

15. The apparatus of claim 14, further comprising a camera and a light source, each in electrical communication with the processor, wherein the camera is configured to obtain an image while the light source is emitting light.

16. The apparatus of claim 14, further comprising a second light source, wherein the first light source is configured to emit visible electromagnetic radiation and the second light source is configured to emit infrared electromagnetic radiation, and wherein the second light source is positioned to generate a retinal reflex in the eye of a subject looking at the target.

17. The apparatus of claim 15, wherein the camera is configured to capture at least one of video data and still image data.

18. A device for processing at least one image for detecting strabismus, the image obtained using an apparatus comprising a light source and a target offset from the light source, the device comprising:
   an input interface configured to receive image data from a camera;
   a memory for storing image data received from the camera; and
   a processor configured to process the image data, for each of the subject's left and right eyes, by
      determining, in the image data, a reflection offset distance, being the distance between a reference point of the eye and a reflection of a light source on the eye,
      determining a difference between the reflection offset distance and a reference reflection offset distance for the corresponding left or right eye, wherein the reference reflection offset distance has been determined based on a relative position of the light source, the target and the subject's head, and
      determining whether the difference is greater than a difference threshold value for detecting strabismus.

19. The apparatus according to claim 15, wherein the camera is configured to obtain an image by the detection of at least one of: infrared electromagnetic radiation, visible electromagnetic radiation and ultraviolet electromagnetic radiation.

* * * * *